United States Patent
Datta et al.

(10) Patent No.: US 9,737,225 B2
(45) Date of Patent: *Aug. 22, 2017

(54) PATCH AND SENSOR ASSEMBLY FOR USE IN MEDICAL DEVICE LOCALIZATION AND MAPPING SYSTEMS

(75) Inventors: Keshava Datta, Chino Hills, CA (US); Eduardo Jimenez, Whittier, CA (US); Rajesh Pendekanti, Chino Hills, CA (US)

(73) Assignee: Biosense Webster, Inc.

(*) Notice: Subject to any disclaimer, the term of this patent is extended or adjusted under 35 U.S.C. 154(b) by 889 days.

This patent is subject to a terminal disclaimer.

(21) Appl. No.: 12/144,826

(22) Filed: Jun. 24, 2008

(65) Prior Publication Data
US 2009/0318796 A1   Dec. 24, 2009

(51) Int. Cl.
  *A61B 5/06* (2006.01)
  *A61B 5/0416* (2006.01)
  *A61B 5/0408* (2006.01)

(52) U.S. Cl.
  CPC ........ *A61B 5/0416* (2013.01); *A61B 5/04087* (2013.01); *A61B 5/06* (2013.01)

(58) Field of Classification Search
  CPC ...... A61B 5/04087; A61B 5/0416; A61B 5/06
  USPC .................. 600/372–397, 407–480
  See application file for complete search history.

(56) References Cited

U.S. PATENT DOCUMENTS

| | | | |
|---|---|---|---|
| 240,166 A | 4/1881 | Nettleton | |
| 3,606,881 A | 9/1971 | Woodson | |
| 3,829,826 A | 8/1974 | Brown et al. | |
| 4,112,941 A * | 9/1978 | Larimore | 600/394 |
| 4,209,020 A | 6/1980 | Nielsen | |

(Continued)

FOREIGN PATENT DOCUMENTS

| CA | 2762280 A1 | 6/2012 |
|---|---|---|
| EP | 1854405 A1 | 11/2007 |

(Continued)

OTHER PUBLICATIONS

EP Search Report No. EP 11 17 8894 Dated Oct. 21, 2011.
(Continued)

*Primary Examiner* — Jennifer Dieterle
*Assistant Examiner* — Vani Gupta

(57) ABSTRACT

An patch and sensor assembly for use in an EP mapping system has two portions: a reusable portion and a disposable portion. The reusable portion houses the biosensors used in magnetic based location and mapping systems and the electrical lead necessary to communicate between the biosensor and the mapping system. The reusable portion may also contain a portion of the electrode necessary to receive electrical signals from the body of the patient. The disposable portion of the patch and sensor assembly contains an adhesive covered flexible patch having at least a portion of the electrode used to receive electrical signals form the body of the patient and may contain the electrical lead necessary to communicate such an electrical signal to the mapping system. The disposable portion contains a receptacle adapted to receive and mechanically secure the reusable portion to the disposable portion of the assembly. Such a patch and sensor assembly is useful in hybrid magnetic and impedance based location and mapping systems such as those used in electrophysiology.

17 Claims, 5 Drawing Sheets

(56) References Cited

U.S. PATENT DOCUMENTS

| | | | |
|---|---|---|---|
| 4,490,005 A | 12/1984 | Hovey | |
| 4,635,642 A | 1/1987 | Cartmell et al. | |
| 4,653,503 A | 3/1987 | Heath | |
| 4,685,467 A | 8/1987 | Cartmell et al. | |
| 4,827,939 A * | 5/1989 | Cartmell et al. | 600/392 |
| 4,947,846 A | 8/1990 | Kitagawa et al. | |
| 5,199,432 A | 4/1993 | Quedens et al. | |
| 5,265,579 A | 11/1993 | Ferrari | |
| 5,355,883 A | 10/1994 | Ascher | |
| 5,391,199 A | 2/1995 | Ben-Haim | |
| 5,443,489 A | 8/1995 | Ben-Haim | |
| 5,467,768 A | 11/1995 | Suda et al. | |
| 5,499,628 A | 3/1996 | Wright | |
| 5,571,165 A * | 11/1996 | Ferrari | 607/142 |
| 5,615,674 A | 4/1997 | Maurer | |
| 5,782,761 A | 7/1998 | Gusakov | |
| 5,879,373 A * | 3/1999 | Roper et al. | 600/344 |
| 5,928,142 A | 7/1999 | Cartmell et al. | |
| 5,978,693 A | 11/1999 | Hamilton et al. | |
| 6,117,077 A | 9/2000 | Del Mar et al. | |
| 6,129,668 A | 10/2000 | Haynor et al. | |
| 6,324,432 B1 | 11/2001 | Rigaux et al. | |
| 6,381,485 B1 | 4/2002 | Hunter et al. | |
| 6,546,271 B1 | 4/2003 | Reisfeld | |
| 6,650,922 B2 | 11/2003 | Kurata et al. | |
| 6,690,963 B2 | 2/2004 | Ben-Haim et al. | |
| 6,780,065 B2 | 8/2004 | Schwarz | |
| 6,788,967 B2 | 9/2004 | Ben-Haim et al. | |
| 6,912,414 B2 | 6/2005 | Tong | |
| 7,104,801 B1 | 9/2006 | Brodnick et al. | |
| 7,110,804 B2 * | 9/2006 | Baumer et al. | 600/372 |
| 7,226,299 B2 | 6/2007 | Pereira et al. | |
| 7,366,562 B2 * | 4/2008 | Dukesherer et al. | 600/424 |
| 7,395,105 B2 | 7/2008 | Schmidt et al. | |
| 7,756,576 B2 | 7/2010 | Levin | |
| 2005/0015134 A1 | 1/2005 | Carim | |
| 2005/0124902 A1 * | 6/2005 | Baumer et al. | 600/509 |
| 2006/0149146 A1 * | 7/2006 | Schmidt et al. | 600/372 |
| 2006/0167354 A1 | 7/2006 | Muller et al. | |
| 2007/0016007 A1 * | 1/2007 | Govari et al. | 600/424 |
| 2007/0225593 A1 * | 9/2007 | Porath | A61B 5/06 600/423 |
| 2008/0114220 A1 | 5/2008 | Banet et al. | |
| 2008/0132773 A1 * | 6/2008 | Burnes et al. | 600/394 |
| 2008/0288026 A1 | 11/2008 | Cross et al. | |
| 2009/0156926 A1 | 6/2009 | Messerly et al. | |
| 2009/0227857 A1 | 9/2009 | Rowe et al. | |
| 2009/0318793 A1 | 12/2009 | Datta et al. | |
| 2009/0318796 A1 | 12/2009 | Datta et al. | |
| 2013/0023750 A1 | 1/2013 | Callahen | |

FOREIGN PATENT DOCUMENTS

| | | |
|---|---|---|
| JP | 6319712 A | 11/1994 |
| JP | 9131328 A | 5/1997 |
| JP | 10230016 A | 9/1998 |
| JP | 2001506154 A | 5/2001 |
| JP | 2007-61612 A | 3/2007 |
| NL | 1019789 C2 | 7/2003 |
| WO | WO 90/01224 A1 | 2/1990 |
| WO | WO 92/08407 A1 | 5/1992 |
| WO | WO 2007/063436 A1 | 6/2007 |
| WO | WO 2008/068695 A1 | 6/2008 |

OTHER PUBLICATIONS

EP Search Report No. EP 12 17 7381 Dated Sep. 28, 2012.
Search Report issued by the People's Republic of China dated Mar. 21, 2013 for corresponding Patent Application No. 200980133806.5.
Japanese Notification of Reasons for Refusal dated Mar. 11, 2014 of corresponding Japanese Patent Application No. 2011-516477.
International Search Report dated Jan. 26, 2010 in corresponding International Application No. PCT/US2009/047995.
Japanese Notification of Reasons for Refusal dated Jul. 9, 2013 in corresponding Japanese Application No. 2011-516477.
Examiner's Requisition dated Oct. 19, 2015 from corresponding Canadian Patent Application No. 2,723,536.
Pending U.S. Appl. No. 12/977,881, filed Dec. 23, 2010.

* cited by examiner

PATCH AND SENSOR ASSEMBLY FOR USE IN MEDICAL DEVICE LOCALIZATION AND MAPPING SYSTEMS

FIELD OF THE INVENTION

The present invention relates to mechanisms for the attaching a reusable cable and housing containing a biosensor for magnetic field based localization to a conductive and adhesive patch assembly having at least a portion of an electrode used for electrical and mechanical contact with the body surface of a patient. More particularly, the invention relates to a patch and cable attachment mechanism optimized for use in an electrophysiology mapping and ablation system using both biosensors and electrodes for magnetic and impedance or current based localization and mapping of medical devices in the human body.

BACKGROUND OF THE INVENTION

Many abnormal medical conditions in humans and other mammals have been associated with disease and other aberrations along the lining or walls that define several different body spaces. In order to treat such abnormal conditions of the body spaces, medical device technologies adapted for delivering various therapies to the body spaces using the least invasive means possible.

As used herein, the term "body space," including derivatives thereof, is intended to mean any cavity within the body which is defined at least in part by a tissue wall. For example, the cardiac chambers, the uterus, the regions of the gastrointestinal tract, and the arterial or venous vessels are all considered illustrative examples of body spaces within the intended meaning.

The term "vessel," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of vessels within the intended meaning. Blood vessels are also herein considered vessels, including regions of the vascular tree between their branch points. More particularly, the pulmonary veins are vessels within the intended meaning, including the region of the pulmonary veins between the branched portions of their ostia along a left ventricle wall, although the wall tissue defining the ostia typically presents uniquely tapered lumenal shapes.

One means of treating body spaces in a minimally invasive manner is through the use of catheters to reach internal organs and vessels within a body space. Electrode or electrophysiology (EP) catheters have been in common use in medical practice for many years. They are used to stimulate and map electrical activity in the heart and to ablate sites of aberrant electrical activity. In use, the electrode catheter is inserted into a major vein or artery, e.g., the femoral artery, and then guided into the chamber of the heart that is of concern in order to perform mapping and ablation procedures. It is important to know and be able to map the location of the tip or other portions of such electrode catheters within the vessels or other locations in the body space.

U.S. Pat. Nos. 5,391,199, 5,443,489, 6,788,967 and 6,690,963 to Ben-Haim, whose disclosures are incorporated herein by reference, describe systems wherein the coordinates of an intrabody probe are determined using one or more field sensors, such as a Hall effect device, coils, or other antennae carried on the probe. Such systems are used for generating three-dimensional location information regarding a medical probe or catheter. Preferably, a sensor coil is placed in the catheter and generates signals in response to externally applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

In United States Patent Application No. 2007/0016007 filed by Govari and incorporated herein by reference, a hybrid position sensing system includes a probe adapted to be introduced into a body cavity of a subject. The probe includes a biosensor having a magnetic field transducer and at least one probe electrodes. A control unit is configured to measure position coordinates of the probe using the magnetic field transducer of the biosensor. The control unit also measures an impedance between the at least one probe electrodes and one or more points on a body surface of the subject. Using the measured position coordinates, the control unit calibrates the measured impedance.

Thus, in such a hybrid magnetic and impedance based systems, a biosensor and electrode must be placed at multiple points on the boy surface of the patient. Because the biosensors and the electrical cabling connecting them to the EP mapping system are relatively expensive, it is ideal that the biosensors and the associated cable be reusable. The portion attached to the skin is preferably disposable, therefore, a disposable patch is necessary for affixing the reusable biosensor and possibly a portion of the electrode to the skin of the patient.

Existing patches comprises one or more stainless steel studs, foam and a conductive adhesive gel that is in contact with the skin of the patient. The matching patch cable in existing systems primarily comprise one ore more matching stainless steel snaps into which the studs of the patch mate, a biosensor and the associated electrical cable all housed in an epoxy shell. Existing biosensor cable and patch mechanisms are radiopaque, i.e., the stainless steel snaps and studs appear on fluoroscopy. When multiple snaps are used which is often the case in order to provide a secure and non-rotating connection between the patch and the sensor cable, the multiple snaps do not allow the patch to take the shape of the body. Also, the patches are often large and conflict with other patches used on the body for ECG, defibrillators, intra-cardiac echograms, etc.

Prior art mechanisms do not provide an adequate solution. For example, U.S. Pat. No. 3,606,881, relates to a disposable patch having a metallic terminal with an enlarged head which permits a squeeze activated clip to be secured around the metallic terminal. U.S. Pat. No. 3,829,826 provides a mechanical mechanism for attaching to the standard male metallic snap of the standard ECG patch. U.S. Pat. No. 4,490,005 relates to a patch in which the central stud is a metal coated non-metallic substrate and which permits rotation of the sensor cable while reducing the effect of rotation on the metal to metal connection. U.S. Pat. No. 4,635,642 relates to a disposable pad in which a conductive, preferably, silver coated metallic stud is inserted in order to make electrical conduct with a gel matrix that is in contact with the skin of the patient.

A similar conductively coated electrically conductive plastic is provided in U.S. Pat. No. 5,499,628 as an eyelet that is press fit into a terminal made of a resilient nonmetallic composition such as polypropylene blended with carbon fiber.

U.S. Pat. No. 5,615,674 relates to a clamping contact connection for contacting a fetal scalp probe.

U.S. Pat. No. 5,782,761 relates to a molded electrode one-piece and two piece constructions for a molded electrode made of a conductive material such as a carbon-filled plastic.

U.S. Pat. No. 6,650,922 relates to an electrode element made of an electrode made of a biodegradable material that is also electro conductive.

U.S. Pat. No. 6,780,065 relates to a device for electrical connection of the power lead to an electrode for use on the skin.

U.S. Pat. No. 7,226,299 relates to a circular electrical connector that engages the socket of a female connector that may include a locking device having resilient prongs.

Design Pat. 240,166 relates to a medical electrode with a rectangular cube portion.

U.S. Patent Application Publication No. 2006/0167354 relates to a system for connecting an electrode to a conductive cable.

U.S. Patent Application Publication No. 2006/0149146 relates to a device having an electrode for contact with the patient and a pressure sensor.

U.S. Pat. No. 5,978,693 relates to an electrode having a deformation sensor such as a strain gauge.

It is an object of the present invention to provide a patch that is generally not visible under fluoroscopy.

It is a further object of the present invention that the patch be capable of being smaller than currently used patches so as to minimize the amount of space used on the skin of the patient and reduce potential conflict with other patches.

Additionally, it is an object of the present invention to provide a patch and sensor cable that will not rotate as would previous designs utilizing a single snap.

Furthermore, it is an object of the present invention to have a patch and sensor cable attachment mechanism that is easy to attach.

Additionally, it is an object of the present invention to have a patch and sensor cable design that could be used for ECG or other instrument systems.

Finally, it is an object of the present invention to have a patch and sensor cable attachment mechanism that enables repeated reuse of the biosensor and sensor cable without any degradation in performance.

SUMMARY OF THE INVENTION

The present invention generally relates to an electrode patch and magnetic sensor assembly for use in an electrophysiology mapping and ablation system. More specifically, the present invention relates to a patch and sensor assembly in which a magnetic-based biosensor is housed in a reusable portion that connects to the mapping and localization system whereas at least a portion of the electrode is in a disposable patch assembly.

More specifically the present invention discloses a patch and sensor assembly for use in a device mapping system used to map the location of a device within the body of a patient comprising a reusable portion and a disposable portion. The reusable portion includes a magnetic-based biosensor for providing location information about the location of the device within the body of the patient to the device mapping system, a housing adapted to house the biosensor and a first electrical lead for communicating an electrical signal from the biosensor to the device mapping system. The disposable portion comprises an adhesive hydrogel layer for adhering the electrode to the body of the patient, an electrode layer disposed on the adhesive hydrogel layer, a foam layer disposed on a portion of the electrode layer; and an engagement element adapted to detachably receive at least a portion of the housing of the reusable portion.

The reusable portion of the patch and sensor assembly of the present invention may also include an electrode element capable of making electrical contact with the electrode layer of the disposable portion. This electrode element would then be connected to a second electrical lead for communicating an electrical signal from the electrode element to the device mapping system. The electrode element may be carbon fiber coated on at least one dimension with a conductive metallic material such as is silver chloride. Other materials such as copper, gold, platinum, or silver may also be used as the reusable electrode element and silver, gold or platinum may also be used as the conductive coating.

Rather than have a conductive cable from the electrode element in the reusable portion, the disposable portion may include second electrical lead for communicating an electrical signal to the device mapping system.

Alternatively, the disposable portion of the patch and sensor assembly may have a second electrical lead for communicating an electrical signal to a third electrical lead in the reusable portion wherein said third electrical lead communicates said electrical signal to the device mapping system.

The foam layer of the patch and sensor assembly may have at least one indentation adapted to receive the sensor housing and sensor cable. Multiple indentations permit various orientations of the sensor housing and cable.

The sensor housing is comprised of a polymer preferably from the group consisting of polyamide, polyurethane, nylon, PEBAX and PEEK polymers and blends thereof.

The reusable portion of the patch and sensor assembly may further comprise a strain relief element for reducing mechanical strain on the connection between the biosensor and the sensor cable.

The disposable portion of the patch and sensor assembly includes one or more arcuate lips adapted to engage a ridge on the sensor housing of the reusable portion in a snap-fit manner. In an alternate embodiment the engagement element of the disposable portion comprises one or more flexible engagement members adapted to engage one or more indentations in the sensor housing.

Alternatively, the reusable portion includes a second engagement element adapted to engage the engagement element of the disposable portion such as a mechanical snap.

DETAILED DESCRIPTION OF THE INVENTION

Figure 1:
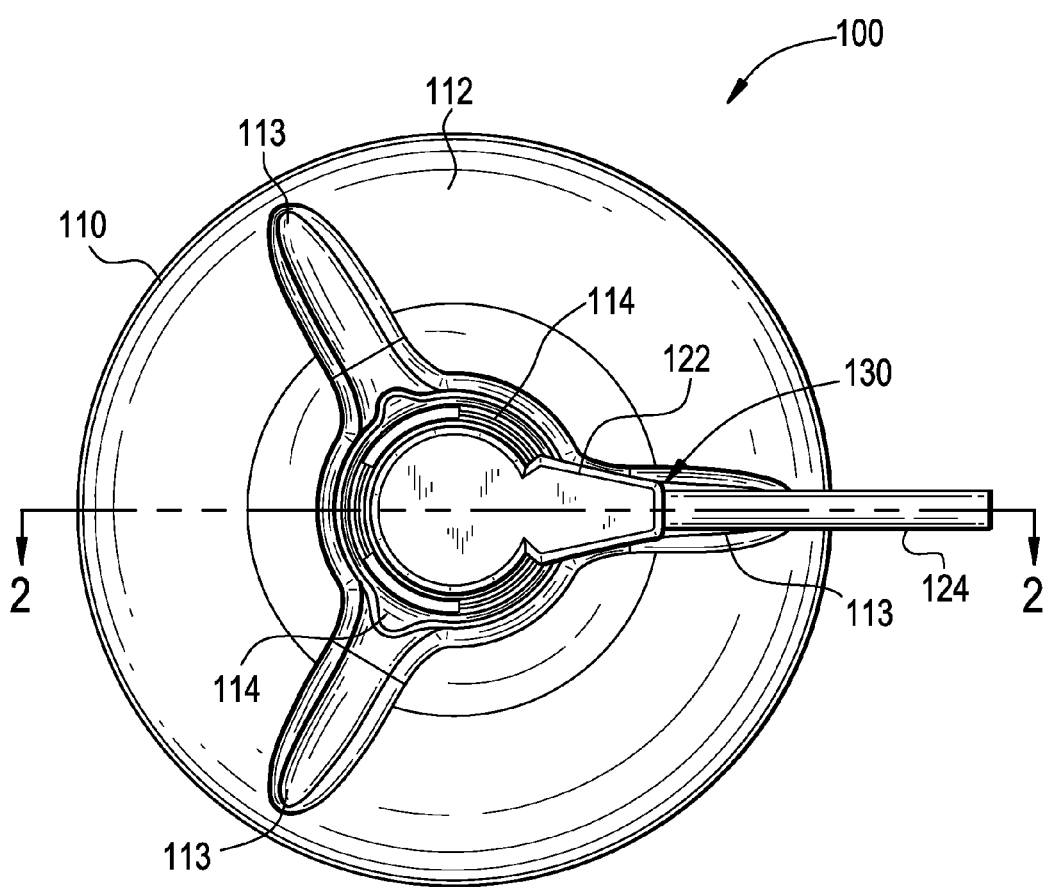
FIG. 1 is a planar view of the top of the patch and sensor cable assembly in accordance with a first embodiment of the present invention.

Referring to the drawings, FIG. 1 depicts a planar view of an embodiment of the patch and sensor cable assembly in accordance with the present invention. As shown in FIG. 1, the patch and sensor assembly 100 comprises two major components: a patch assembly 110 and a sensor cable assembly 130. Sensor cable assembly 130 comprises a sensor housing 122 that is adapted to connect to the patch assembly 110 and a sensor cable 124. In FIG. 1 the connection between the sensor housing 122 and patch assembly 110 is a snap-fit based on the engagement of ridge 123 of sensor housing 122 and the lip of engagement element 114 of patch assembly 110. Patch assembly 110 comprises a foam disk 112 having a plurality of indentations 113 adapted to receive the sensor cable 124. The patch assembly in FIG. 1 is shown with three such indentations enabling a user to attach the sensor cable assembly in one of three positions even after the disposable patch assembly has been placed on the patient. One or more such indentations 113 may be used with the upper limit constrained by the ability of the remaining engagement element 114 to securely engage the ridge 123 of sensor housing 122. Engagement element 114 contains indentations that match those in foam disk 112. The foam used to form foam disk 112 may be any suitable material such as thermofoam, any elastomers like rubbber, santoprene, polyurethane etc. and is preferably thermofoam.

Figure 2:
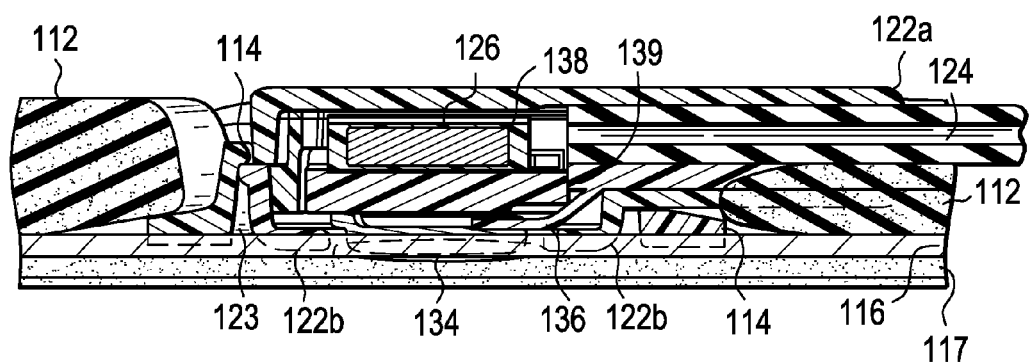
FIG. 2 is a partial cross-sectional view of the patch and sensor cable assembly of FIG. 1 through line A-A.

FIG. 2 depicts a partial cross-section of the patch and sensor assembly of FIG. 1 taken through line A-A. Foam disk 112 rests on a carbon film disk 116 coated with a layer of silver chloride on both sides. Carbon film disk 116 is approximately 0.5 mm in thickness and the layer of silver chloride is approximately 0.1 mm in thickness. Other thicknesses of carbon film disk 116 and silver chloride coating may be used without departing from the spirit of the invention. On the patient facing side of carbon film disk 116 is a hydrogel layer 117. Hydrogel layer 117 is comprised of a conductive gel medium, which also has adhesive properties to the skin, preferably a hydrogel being a mix of Silver/Silver Chloride with water based compound and is approximately 1 mm mm in thickness.

Foam disk 112, carbon film disk 116 and the hydrogel layer 117 generally have approximately the same diameter which should be large enough to provide a secure attachment to the body surface of the patient and is preferably between 4 cm and 16 cm. The only other component of patch assembly 110 is the engagement element 114. Patch assembly 110 comprises only low-cost components in order to increase the disposability of the patch assembly in this embodiment.

The other component of the patch and sensor assembly 100 depicted in FIGS. 1 and 2 is the reusable sensor cable assembly 130. The reusable sensor cable assembly 130 comprises the aforementioned sensor housing 122. Sensor housing 122 is a two-piece design in which upper housing portion 122a is design to fit together with lower housing portion 122b. Lower housing portion 122b contains the ridge 123 that engages engagement element 114 of the patch assembly although this ridge could be disposed on the upper housing portion without departing from the spirit of the present invention. Sensor housing 122 is comprised of a polymer such as ABS, nylon, polypropylene or other suitable polymer known in the art and is preferably made from polypropylene. Sensor housing 122 could be comprised of more than two parts without departing from the spirit of the invention.

Sensor cable assembly 130 further comprises the sensor cable 124 which comprises a conductive ACL cable made of a conductive and flexible material, preferably 28 gauge braided copper wire, three twisted pair conductors for the biosensor has along with two Kevlar fibers for added strength inside a polymeric outer sheath. One wire in sensor cable 124 is welded or bonded using a conductive epoxy to biosensor 126.

Sensor cable assembly 130 further comprises active current location (ACL) disk 134 which may be made of a suitably conductive material and is preferably a generally circular carbon disk coated with silver chloride. Gold or platinum may also be used instead of silver chloride for the coating and the carbon disk could be replaced with a polymer such as ABS or polycarbonate with or without carbon fibers embedded therein. ACL cable 136 is attached to ACL sensor 134 using a suitable conductive epoxy, preferably any epoxy preferably embedded silver particles. In use, current flowing through the patient is conducted through the hydrogel layer 117, carbon film disk 116 to ACL sensor 134 and through ACL cable 136 to the localization and mapping system that uses the ACL information to perform localization and mapping functions in accordance with United States Patent Application No. 2007/0016007 filed by Govari and incorporated herein by reference or other such similar system.

Sensor cable assembly 130 further comprises biosensor 126 which is a biosensor implemented in accordance with one or more of U.S. Pat. Nos. 5,391,199, 5,443,489, 6,788, 967 and 6,690,963 to Ben-Haim, whose disclosures are incorporated herein by reference. Magnetic field based information from biosensor 126 is an electrical current induced by the magnetic field in which the patient is placed and is used in a manner similar to that used in the Carto™ EP mapping systems manufactured and sold by Biosense Webster, Inc. The electrical current from biosensor 126 is conducted through three twisted pair conductors of the sensor cable assembly 130 to biosensor cable which connects to and EP mapping and localization system where the information is used. Biosensor 126 is housed in biosensor housing 138. Isolation layer 139 is thin piece of plastic material preferably polypropylene, ABS or polycarbonate which isolates the 4 KV defibrillation pulse from ACL wire to the biosensor 126.

As can be seen from FIGS. 1 and 2, it is advantageous to have the biosensor 126, ACL sensor 114 and the sensor cable 124 in the reusable sensor cable assembly 130 in order to reduce the cost of the disposable patch assembly 110. The sensor cable assembly 130 is connected to the patch assembly using an easy to operate snap-fit connection. This force will hold the re-usable to the disposable part. The sensor cable assembly may be positioned in one of several orientations around the central axis of the patch assembly but rotation is prohibited by the combination of the engagement element 114 and the matching indentations in the foam disk 112.

Figure 3:
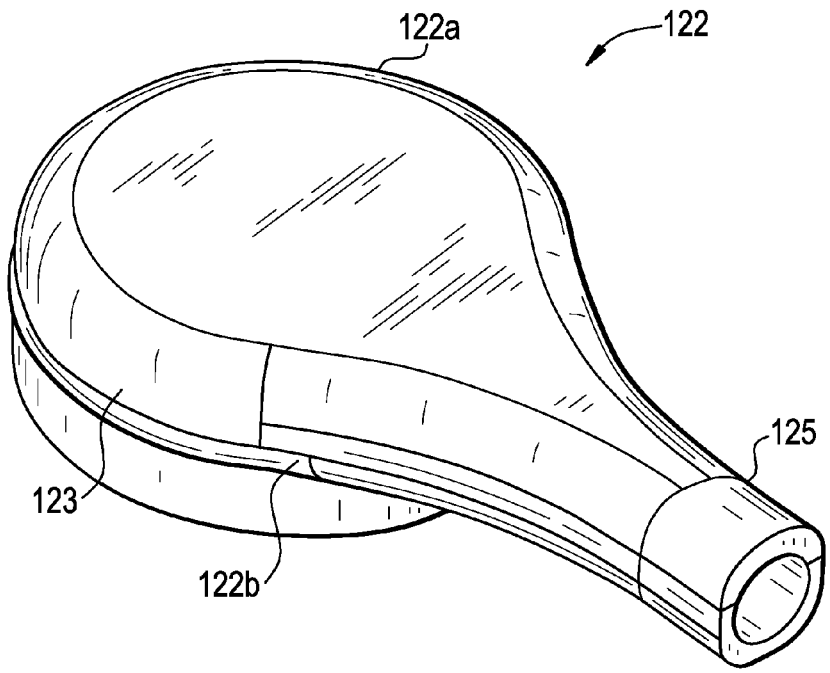
FIG. 3 is a perspective view of the strain relief element for use in patch and sensor cable assembly of FIG. 1.

FIG. 3 depicts a perspective view of the sensor housing 122 showing the upper sensor housing 122a, the lower sensor housing 122b and the ridge 123. Sensor assembly 122 preferably includes the strain relief element 125 but may also be substantial circular without such element. Strain relief element 125 may be integral with sensor housing 122 or may comprise a separate polymeric sleeve that covers a portion of sensor cable 124.

Figure 4:
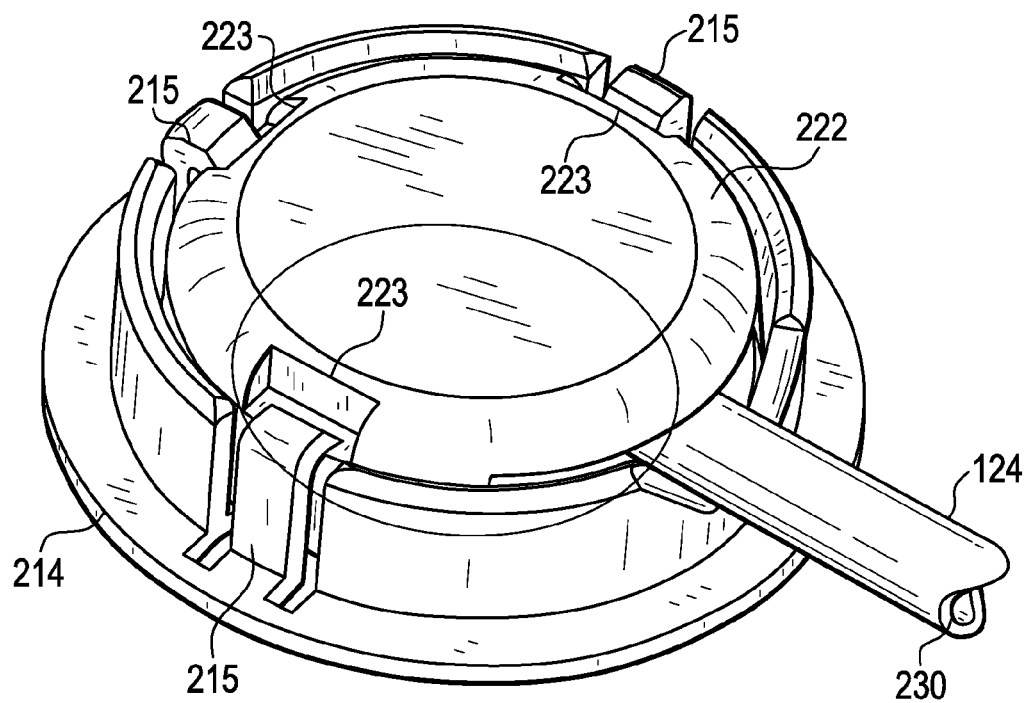
FIG. 4 is a perspective view of a second embodiment of a patch and sensor cable connector in accordance with the present invention.
Figure 5:
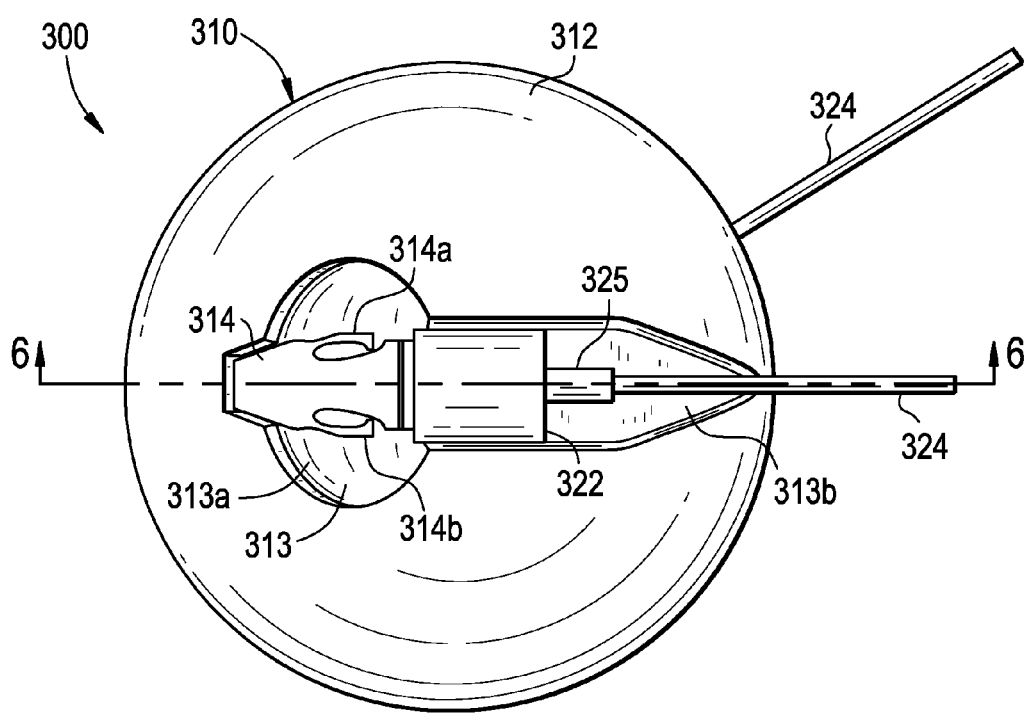
FIG. 5 is a planar view of the top of a further embodiment of a patch and sensor cable assembly in accordance with the present invention.
Figure 6:
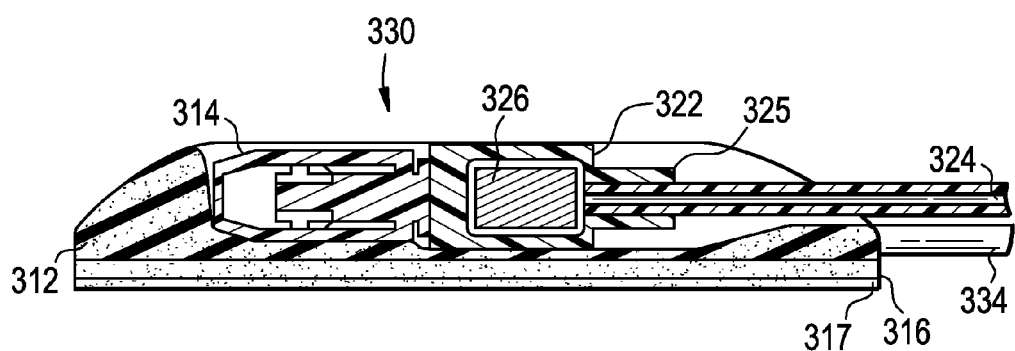
FIG. 6 is a cross-sectional view of the embodiment of the patch and sensor cable assembly of FIG. 5.

FIG. 4 depicts a perspective view of a further embodiment of a patch and sensor cable connector in accordance with the present invention. Sensor housing 222 has a plurality of indentations 223 which are adapted to engage under flexible engagement members 215 which form a portion of engagement element 214. As in the previous embodiment described above, sensor housing 222 forms a part of a sensor cable assembly 230 and engagement element 214 form a part of the patch assembly 110. Engagement element 214 is made from a polymer that is sufficiently flexible to enable flexible engagement members 215 to be pushed toward the periphery while the sensor cable assembly 230 is inserted into the engagement element 214. The snap of re-useabable to disposable part is held using a cantilever beam tab. The disposable part will have the lever which deflects during the snapping operation. The normal forces exherted from the cantilever beam hold the snap together FIGS. 5 and 6 depict a planar top view and cross sectional view of another embodiment of a patch and sensor assembly in accordance with the present invention. Patch and sensor assembly 300 comprises two portions: a patch cable assembly 310 and a sensor cable assembly 330. Patch cable assembly 310 comprises a foam disk 312 having indentation 313 (with portions 313a and 313b) to accommodate the sensor housing 322 and engagement element 314. Two separate cables are used to connect the biosensor and ACL sensor to the mapping and localization system. ACL cable 334 is used to connect the ACL sensor layer 316 to the system for transmittal of current information to the localization system. Alternatively, the ACL cable 334 can be substantially shorter than the length necessary to reach to the mapping and localization system and can be adapted to have a fitting that is designed to connect to a mated fitting on a cable that is collinear with the sensor cable. In the configuration, the fitting on the ACL cable is attached to the fitting on the additional cable that forms part of the sensor cable. In this manner, a substantial length of the ACL cable becomes part of the reusable sensor cable assembly. ACL cable 334 is stranded 28 gauge wire that is sandwiched between the foam disk 312 and the ACL sensor layer 316. ACL sensor layer 316 is a silver chloride coated carbon film of approximately 1 mm with a silver chloride coating of approximately 0.5 mm. Below the ACL sensor layer 316 is a hydrogel layer 317 substantially the same as the one described above with respect to the other embodiment.

FIG. 5 has the snap feature in the form of three legs. This feature also works similar to principle of cantilever beam of FIG. 4. The legs deflect on the reusable part conforming to the opening on the disposable side. When snapped the beam expands providing the normal force to hold the two parts together.

Sensor cable assembly 330 comprises the engagement element 314, sensor housing 322 with biosensor 326 mounted inside. Sensor cable 324 is used to connect the biosensor 326 that provides magnetic based localization information to the system. Sensor cable 324 is a 48 gauge braided copper wire coated with a protective polymer with an exposed end welded or bonded, preferably using a conductive epoxy to the biosensor 326. Strain relief element 325 covers a portion of the sensor cable 324 in order to reduce mechanical stress on the connection of the sensor cable to the biosensor and sensor housing. Biosensor 326 is substantially similar to biosensor 126 for the embodiment described above. Engagement element 314 is a mechanical snap designed to engage patch cable assembly 310. Engagement element 314 has moveable elements 314a and 314b that are depressed in order to release and/or engage the engagement element onto the patch assembly.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A patch and sensor assembly for use with a device mapping system capable of mapping a relative location of a device within the body of a patient comprising:
   a reusable portion and a separate disposable portion,
   the reusable portion comprising:
      a magnetic-based biosensor configured to generate magnetic field based location information signals in response to externally applied magnetic fields from at least one magnetic field generator fixed to an external reference frame, and to provide the magnetic field based location information signals to the device mapping system, wherein the magnetic field based location information is indicative of the relative position of the patch and sensor assembly within the external reference frame;
      a housing adapted to house the biosensor;
      a first electrical lead for communicating the magnetic field based information signals from the biosensor to the device mapping system; and,
   the separate disposable portion comprising:
      an adhesive hydrogel layer for adhering the disposable portion to the body of the patient;
      an electrode layer disposed on the adhesive hydrogel layer, the adhesive hydrogel layer and the electrode layer being part of a first electrode element, wherein the first electrode element is configured to conduct and communicate an impedance-based electrical signal directly to the device mapping system, the impedance-based electrical signal is the result of energy flowing through the body of the patient from an interbody-electrode on the device to the first electrode element and is indicative of the location the device within the body relative to the patch and sensor assembly;
   a foam layer disposed on a portion of the electrode layer; and,
      an engagement element adapted to detachably receive at least a portion of the housing of the reusable portion.

2. The patch and sensor assembly of claim 1 wherein the reusable portion further comprises a second electrode element capable of making electrical contact with the first electrode element of the disposable portion.

3. The patch and sensor assembly of claim 2 wherein the reusable portion further comprises a second electrical lead for communicating an electrical signal from the second electrode element to the device mapping system.

4. The patch and sensor assembly of claim 2 wherein the second electrode element comprises carbon fiber coated on at least one dimension with a metallic material.

5. The patch and sensor assembly of claim 4 wherein the metallic material is silver chloride.

6. The patch and sensor assembly of claim 4 wherein the metallic material is selected from the group consisting of: silver chloride, gold and platinum.

7. The patch and sensor assembly of claim 1 wherein the disposable portion further comprises a second electrical lead for communicating an electrical signal to the device mapping system.

8. The patch and sensor assembly of claim 1 wherein the disposable portion further comprises a second electrical lead for communicating an electrical signal to a third electrical lead in the reusable portion wherein said third electrical lead communicates said electrical signal to the device mapping system.

9. The patch and sensor assembly of claim 1 wherein the foam layer comprises at least one indentation adapted to receive the biosensor housing and the first electrical lead.

10. The patch and sensor assembly of claim 1 wherein the sensor housing is comprised of a polymer.

11. The patch and sensor assembly of claim 10 wherein the polymer is selected from the group consisting of polyamide, polyurethane, nylon, PEBAX and PEEK polymers and blends thereof.

12. The patch and sensor assembly of claim 1 wherein the foam layer is comprised of thermofoam.

13. The patch and sensor assembly of claim 1 wherein the reusable portion further comprises a strain relief element for reducing mechanical strain on the connection between the biosensor and the sensor cable.

14. The patch and sensor assembly of claim 1 wherein the engagement element of the disposable portion comprises one or more arcuate lips adapted to engage a ridge on the sensor housing of the reusable portion in a snap-fit manner.

15. The patch and sensor assembly of claim 1 wherein the engagement element of the disposable portion comprises one or more flexible engagement members adapted to engage one or more indentations in the sensor housing.

16. The patch and sensor assembly of claim 1 wherein the reusable portion comprises a second engagement element adapted to engage the engagement element of the disposable portion.

17. The patch and sensor assembly of claim 16 wherein the second engagement element is a mechanical snap.

* * * * *